United States Patent
Guenst

(10) Patent No.: US 7,871,417 B2
(45) Date of Patent: Jan. 18, 2011

(54) TRANSCONDUIT PERFUSION CATHETER AND METHODS FOR PERFUSING A BLOOD VESSEL DURING AN ANASTOMOSIS PROCEDURE

(75) Inventor: Gary W. Guenst, Collegeville, PA (US)

(73) Assignee: Medtronic, Inc., Minneapolis, MN (US)

( * ) Notice: Subject to any disclaimer, the term of this patent is extended or adjusted under 35 U.S.C. 154(b) by 1097 days.

(21) Appl. No.: 10/824,341

(22) Filed: Apr. 14, 2004

(65) Prior Publication Data
US 2005/0234482 A1    Oct. 20, 2005

(51) Int. Cl.
*A61B 17/08* (2006.01)
(52) U.S. Cl. ..................................... 606/153
(58) Field of Classification Search ............... 623/1.14, 623/1.23; 606/108, 153, 191; 128/898; 604/4.01–10, 604/23, 27, 93.01, 507–509, 513, 96.01, 604/103.06, 104
See application file for complete search history.

(56) References Cited

U.S. PATENT DOCUMENTS

| | | | |
|---|---|---|---|
| 4,029,104 A | | 6/1977 | Kerber et al. |
| 4,230,119 A | * | 10/1980 | Blum .......................... 606/194 |
| 4,406,656 A | * | 9/1983 | Hattler et al. ................ 604/523 |
| 4,813,934 A | | 3/1989 | Engelson et al. |
| 5,290,231 A | | 3/1994 | Marcadis et al. |
| 5,417,969 A | | 5/1995 | Hsu et al. |
| 5,505,698 A | * | 4/1996 | Booth et al. ............ 604/103.11 |
| 5,695,504 A | * | 12/1997 | Gifford et al. ................ 606/153 |
| 5,868,764 A | * | 2/1999 | Rosengart .................... 606/153 |
| 5,925,054 A | * | 7/1999 | Taylor et al. ................. 606/153 |
| 5,947,919 A | * | 9/1999 | Krueger et al. .................. 604/8 |
| 6,019,788 A | * | 2/2000 | Butters et al. ............... 623/1.35 |
| 6,042,569 A | * | 3/2000 | Finch et al. .................. 604/175 |
| 6,059,809 A | * | 5/2000 | Amor et al. .................. 606/194 |
| 6,146,358 A | | 11/2000 | Rowe et al. |
| 6,241,741 B1 | * | 6/2001 | Duhaylongsod et al. .... 606/153 |
| 6,585,762 B1 | * | 7/2003 | Stanish ........................ 623/1.3 |
| 6,626,872 B1 | * | 9/2003 | Navia et al. .................. 604/264 |
| 2002/0091398 A1 | * | 7/2002 | Galdonik et al. ............ 606/153 |
| 2002/0123698 A1 | | 9/2002 | Garibotto et al. |
| 2004/0002677 A1 | | 1/2004 | Gentsler |

FOREIGN PATENT DOCUMENTS

EP    1 205 209    5/2002

* cited by examiner

*Primary Examiner*—Melanie Tyson
(74) *Attorney, Agent, or Firm*—Mike Jaro; Jeffrey J. Hohenshell

(57) ABSTRACT

Methods and devices for perfusing a blood vessel during the entire course of an end-to-side or end-to-end anastomosis procedure. One method can be used to form an end-to-side anastomosis of a saphenous vein graft to a coronary artery during an off-pump, beating heart, coronary artery bypass graft. In this example, the distal end of an elongate tube carrying a saphenous vein graft is advanced into an arteriotomy distal to an occlusion in the coronary artery. Perfusing blood flow is provided through the tube to the coronary artery, the vein graft is advanced over the tube to the arteriotomy and sutured completely to the coronary artery. The elongate tube can be retracted through the now secured vein graft, and the coronary artery supplied again from the proximal end of the vein graft. Some tubular devices include a reversibly expandable distal region, to form a seal between the inserted tube and the coronary artery being perfused, to prevent blood flow into the surgical field.

25 Claims, 6 Drawing Sheets

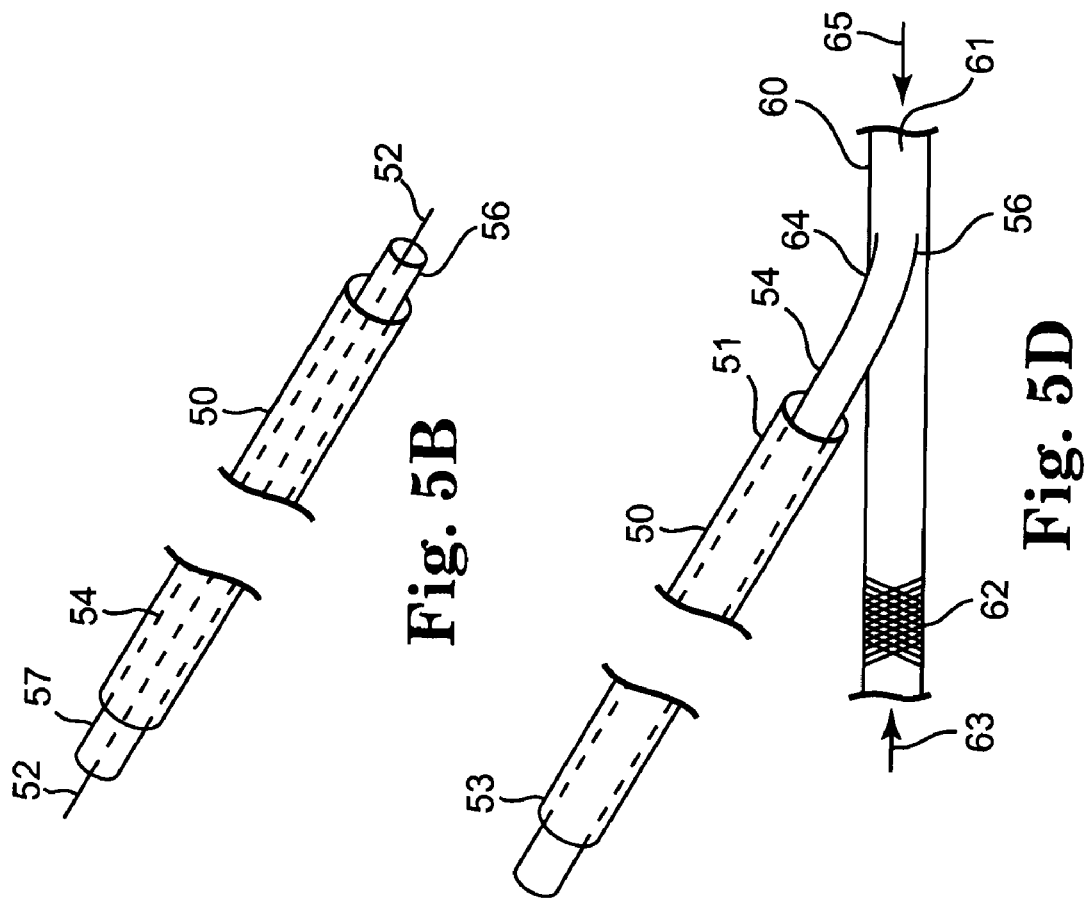
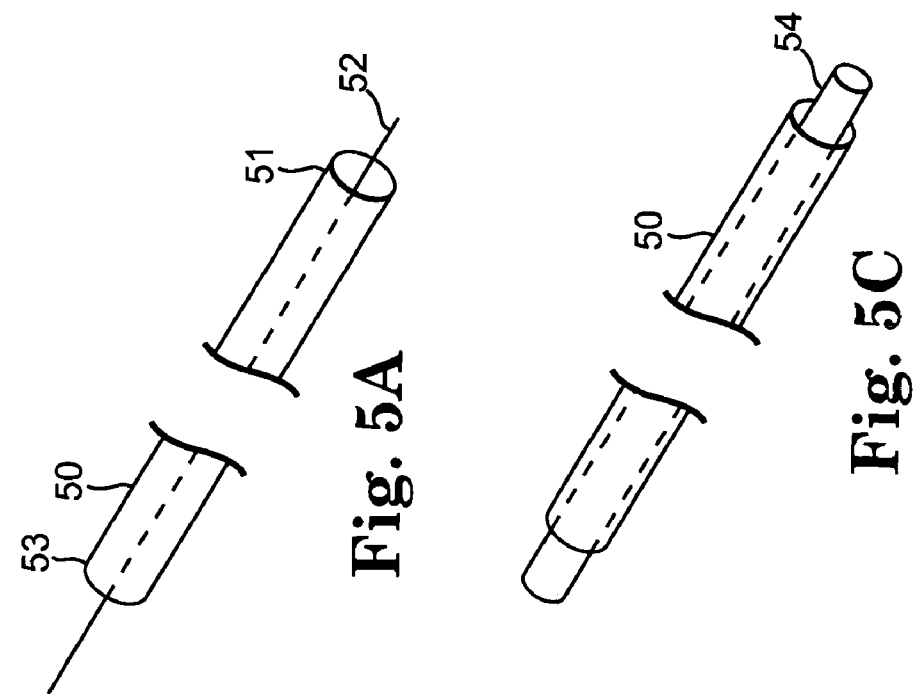
Fig. 5A
Fig. 5B
Fig. 5C
Fig. 5D

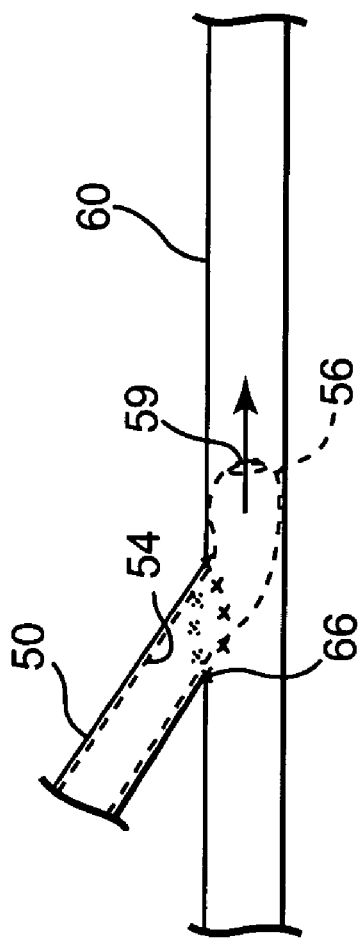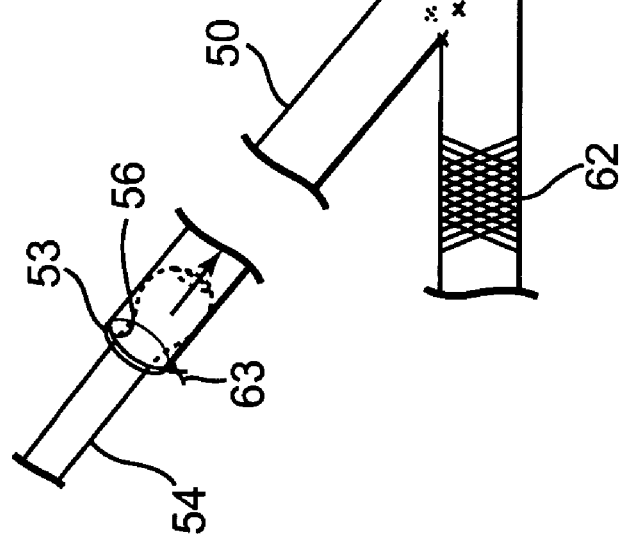
Fig. 5E
Fig. 5F

TRANSCONDUIT PERFUSION CATHETER AND METHODS FOR PERFUSING A BLOOD VESSEL DURING AN ANASTOMOSIS PROCEDURE

FIELD OF THE INVENTION

The present invention is related to medical devices. More specifically, the present invention is related to medical devices that can be used to perform blood vessel anastomosis procedures. The present invention can find one non-limiting use in performing cardiac artery bypass grafts on beating hearts.

BACKGROUND OF THE INVENTION

In coronary bypass surgery, a partially occluded coronary artery can be bypassed by grafting a conduit to the coronary artery to supply perfusing blood, to a location downstream or distal of the occlusion. The conduit is often a saphenous vein graft or an internal mammary artery (IMA). The conduit has a distal end, to be joined distal to the occlusion, and a proximal end, to be joined to a source of perfusing blood, typically the aorta.

In a typical procedure, an incision, an arteriotomy, is made in the coronary artery distal to the occlusion. The incision often results in bleeding through the incision into the surgical field. The blood can be suctioned and/or blown away to preserve the surgeon's field of view. The distal end of the conduit can be brought to bear to the side of the coronary artery near the arteriotomy. An end-to-side anastomosis can then be performed.

In the end-to-side anastomosis, the distal end of the conduit is sewn to the side of the coronary artery over the incision. During the anastomosis procedure, the blood flow from the incision may be quite profuse. The blood may come through the original blood vessel, which may be only partially occluded. The blood may also come from the "collateral flow" of blood coming from the coronary artery distal of the occlusion. The collateral flow can come from vessels that have grown to supply the coronary artery distal of the occlusion, often in response to the occlusion.

The blood flowing from the incision is not flowing to the heart, which can result in ischemia, which can be severe. The ischemia can put additional time pressure on the surgeon. If severe, the ischemia may force the surgeon to put the patient on a blood pump where this was initially to be avoided. In some cases, a planned for minimally invasive beating heart procedure is changed into an open chest, arrested heart procedure, with the patient put onto a heart-lung machine. The blood can also flood the surgical field, interfere with the surgeon's vision, and thus interfere with, and lengthen, the anastomosis procedure.

The ischemia problem has been addressed by off-pump perfusion-assisted direct coronary artery bypass (PAD-CAB™) (Quest Medical, Austin Tex.), using a distal perfusion device. Medtronic (Minneapolis, Minn.) sells the Quick-Flow™ DPS™ Distal Perfusion System. The distal perfusion device includes a tubular member that can be supplied at the proximal end with perfusing blood from the aorta or the femoral artery. The distal end of this device can be inserted into the incision in the artery. The blood flow through the distal perfusion device can supply the coronary artery with some perfusing blood during the anastomosis procedure. The distal perfusion device distal end can be difficult to hold in position during some surgeries, especially minimally invasive surgeries. Blood flow through the incision typically continues, into the surgical field.

When using the distal perfusion device, the sutures required to join the end of the conduit to the coronary artery are begun, but are often initially made very loose, allowing the conduit distal end to be located some distance away from the side of the coronary artery be sutured. The conduit is thus be only partially joined to the coronary artery, while working around the distal perfusion device inserted into the incision in the coronary artery. Working around a tube protruding from the anastomosis site may provide an added, unneeded challenge to the surgeon.

The distal perfusion device can then be withdrawn, and the conduit completely joined to the coronary artery, by adding more sutures and by tightening the previously made sutures. When the distal perfusion device is withdrawn, ischemia may begin and the blood flow into the surgical field worsen. In some situations, the patency of the anastomosis is less than desirable, as the end of the conduit had become at least partially closed or even sewn shut at the anastomosis. This lack of patency is understandable, given the 1-2 millimeter inside diameter of a coronary artery, the blood flow about the anastomosis site, and the time pressure on the surgeon, which is only increased by ischemia.

What would be desirable are devices and methods for perfusing coronary arteries during the entire anastomosis procedure, allowing the anastomosis to be completely formed between a conduit and a coronary artery. What would be advantageous are devices and methods for reducing blood flow through the anastomosis site into the surgical field. Methods for maintaining patency during the anastomosis procedure would also be beneficial.

SUMMARY OF THE INVENTION

The present invention provides methods for joining a blood conduit to a blood vessel. The methods can include making an incision in the blood vessel wall and inserting a tubular member into the conduit. The tubular member carrying the conduit can be advanced into the blood vessel through the incision. The conduit distal region can then be fixedly joined to the vessel wall near the incision, while providing an oxygenated liquid flow through the tubular member disposed within the conduit and into the blood vessel. In some methods, inserting the tubular member within the conduit is performed before advancing the tubular member into the blood vessel, while in other methods, the inserting is performed after the advancing the tubular member into the blood vessel. The fixedly joining can include suturing the conduit to the blood vessel.

In some methods, the blood vessel is a coronary artery, the conduit is a saphenous vein graft, and the method includes fixedly joining the saphenous vein graft to the coronary artery to perform a coronary artery bypass. In other methods, the conduit is a radial artery, or an internal mammary artery (IMA) having both proximal and distal ends available, a xenogenic blood vessel, or an artificial blood vessel. In some methods, the oxygenated liquid is blood, which can be supplied under pressure higher than the patient's own blood pressure. This added pressure can be provided by a spring-loaded, pressure limited syringe, by a manual bulb, or any other suitable device for providing pressurized blood.

In a preferred method, the tubular member has a distal region, which can be reversibly radially expanded to increase the distal region outer diameter once the tubular member has been inserted into the blood vessel. The distal region can be increased in outer diameter to form a seal between the tubular member and the blood vessel being supplied with blood. One tubular member includes a flow restrictor in the distal region and a weakened wall region proximal of the flow restrictor. In this device, providing blood or other oxygenated fluid under pressure through the tubular member increases the pressure in the tube that causes the weakened distal region to expand outward, similar to a balloon. In some methods, blood is supplied from the patient's aorta, while in other methods, the blood is supplied from the patient's femoral artery. In some closed chest procedures, blood can be supplied to the tubular member from the femoral artery, with the tubular member deployed within the chest via a port or simple stab wound.

The present invention finds one use in providing a method for performing an end-to-side anastomosis during a coronary artery bypass graft. In this application of the invention, an arteriotomy is made distal to an occluded or stenosed coronary artery. This may be done off pump, with the patient's heart still beating, even in a minimally invasive procedure. A suitable blood conduit, for example a saphenous vein graft, can be provided, already disposed over the elongate tube of the present invention, also referred to as the transconduit perfusion catheter or TPC. The TPC carrying the saphenous vein graft can be advanced to the arteriotomy, with the distal region of the TPC advanced through the arteriotomy and into the coronary artery away from the stenosis. The distal region of the TPC can then be expanded to form a seal between the distal region of the TPC and the coronary artery. This can reduce or eliminate blood flow through the arteriotomy that can obscure the surgical field. Blood can then be provided to the TPC proximal end, flowing through the TPC and into the coronary artery, thus perfusing the artery during the anastomosis procedure. With the coronary artery being perfused, the saphenous vein graft or other conduit can be advanced over the TPC to the arteriotomy site, and completely sutured to the coronary artery. The TPC can thus act to perfuse the coronary artery, to reduce collateral blood flow into the surgical field, and function as a suture guide, guiding the conduit directly to the arteriotomy site and holding the conduit in position during the suturing.

With the sutures in place, the TPC distal region can be reduced in profile and the TPC proximally retracted through the now secured conduit to the proximal region of the conduit. The conduit can be resupplied with blood by reexpanding the distal region of the TPC and/or by tying a purse-string suture around the proximal end of the conduit, securing it tightly about the TPC within.

The present invention finds another use in providing a method for performing an end-to-end anastomosis of a blood vessel. This application is similar in some respects to the end-to-side anastomosis just described. In this application of the invention, the proximal end of a blood vessel to be extended is made accessible, rather than the arteriotomy just described. The TPC can be inserted into the blood vessel lumen through the proximal end and expanded. The conduit to be joined to the blood vessel can be advanced over the TPC and sutured to the blood vessel.

The present invention also includes a device for providing perfusing blood during an anastomosis. The device can include an elongate tube having a proximal end, a distal region, a distal end, an outside diameter, and a length. The outside diameter can be less than about two millimeters and the length less than about 25 centimeters. The distal region can have a flow restrictor and a weakened distal wall region proximal to the flow restrictor. Increasing the fluid flow through the tube can cause the weakened wall region to expand radially outward to increase the outer diameter of the distal wall region. The weakened wall region is weaker than the remainder of the tube wall in a preferred embodiment. This weaker wall region can be provided by making the weakened wall region of a weaker material, a thinner material, or a scored material. The elongate tube can have an anti-thrombogenic, thrombolytic, and/or heparin-containing coating on the outer and/or inner surfaces of the tube, depending on the embodiment. A lubricious coating may also be provided on the inner and/or outer surfaces, again depending on the embodiment.

DESCRIPTION OF THE DRAWINGS

FIG. 5A is a fragmentary, perspective view of a conduit having a stylet inserted therethrough;

FIG. 5B is a fragmentary, perspective view of the conduit and stylet of FIG. 5A after the transconduit perfusion catheter of FIG. 1 has been inserted over the stylet and within the conduit;

FIG. 5C is a fragmentary, perspective view of the conduit and transconduit perfusion catheter of FIG. 5B, after the stylet has been removed;

FIG. 5D is a fragmentary, cut-away view of a blood vessel having the transconduit perfusion catheter advanced through an opening in the side of the blood vessel;

FIG. 5E is a fragmentary, side view of the blood vessel of FIG. 5D, having the transconduit perfusion catheter distal region expanded within and the anastomosis sutures fully completed;

FIG. 5F is a fragmentary, side view of the blood vessel and conduit of FIG. 5E, after the transconduit perfusion catheter has been moved to proximally supply the conduit;

DETAILED DESCRIPTION OF THE PREFERRED EMBODIMENTS

Figure 1:
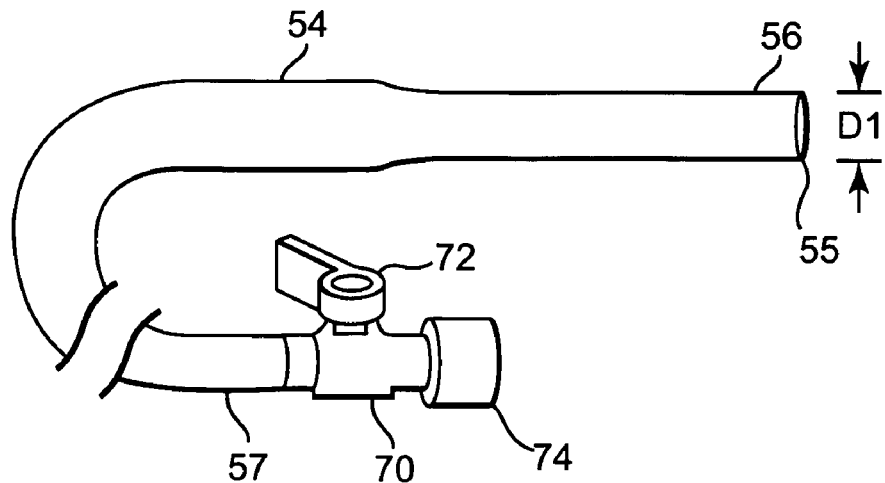
FIG. 1 is a fragmentary, side view of a transconduit perfusion catheter having a valve at the proximal end.

FIG. 1 illustrates a transconduit perfusion catheter (TPC) 54 having generally a distal region 56, a distal tip 55, and a proximal region 57. In the embodiment illustrated, TPC 54 also has a valve 70 coupled to proximal region 57 and a handle 72 for opening and closing the valve. A piece of standard arterial tubing 74 is coupled to valve 70 as well. TPC 54 is adapted to be inserted into a vessel for which an end-to-side anastomosis is to be performed. In one application, TPC 54 is to be inserted into an arteriotomy in a coronary artery. In this example, TPC 54 can have an outer diameter, indicated at D1, of less than 2 millimeters in some embodiments, less than 1.5 millimeters in other embodiments, and between about 1 millimeter and 1.5 millimeters in various embodiments. TPC 54 has a lumen extending therethrough, for carrying a perfusing, oxygen carrying fluid.

Figure 2:
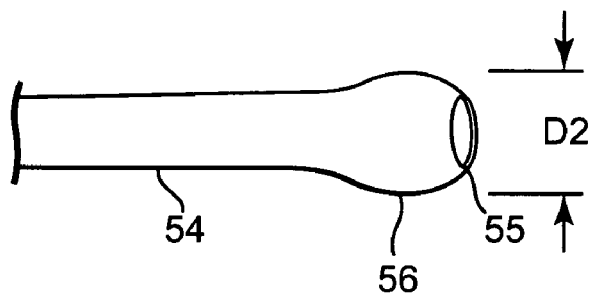
FIG. 2 is a fragmentary, side view of the distal portion of the catheter of FIG. 1, shown in an expanded configuration.

FIG. 2 illustrates TPC 54 in one embodiment, having a distally expandable or swellable distal region 56. Distal region 56 is preferably reversibly swellable or reversibly expandable to have an increased outer diameter, indicated at D2, relative to D1 of FIG. 1. TPC distal region 56 can be increased in outer diameter after being inserted into a blood vessel, to provide a better seal between the outer surface of the TPC and the inner surface of the blood vessel to be perfused. In one embodiment, distal region 56 is made reversibly expandable by disposing a flow restrictor downstream of the region to be reversibly expanded in diameter. In one example, this flow restrictor is disposed near distal tip 55 of TPC 54. Distal region 56 can be made to expand upon the application of increased pressure making region 56 weaker or more elastic relative to the more proximal region in some embodiments, and optionally weaker or more elastic than some more distal wall regions in other embodiments.

In some embodiments, distal region 56 is made reversibly swellable by making it of a different material, being more elastic than the more proximal, and possibly, more distal regions. Distal region 56 may simply be weaker, being made of a softer durameter material, and being joined to harder durameter materials proximal of the distal region material. In other embodiments, distal region 56 is made to be reversibly expandable upon the application of pressure by making the wall thickness less than in the more proximal region. Distal region 56 could also be scored to make this region weaker and more likely to expand under pressure than the surrounding, nonscored areas. In still another embodiment, the TPC can be configured to be expanded, for example as shown in FIG. 2, in an unconstrained state, and made or forced to assume a narrower profile after inserting a stylet through the transconduit perfusion catheter to stretch the catheter lengthwise.

TPC 54, in one example, which can be used in open chest coronary bypass procedures, has a length of less than 25 centimeters, and can be between 22 and 25 centimeters. TPC 54 can be formed of any suitable biocompatible tubing material, well known to those skilled in the art. In some examples, TPC 54 is formed of silicone rubber, or polyurethane. TPC 54 can be coated externally and/or internally with an anti-thrombogenic or thrombolytic material, for example, Carmeda (TM), or a heparin coating. TPC 54 may also be coated with a lubricious, for example, hydrophilic material on the interior, and/or exterior surfaces, depending on the embodiment.

Figure 3:
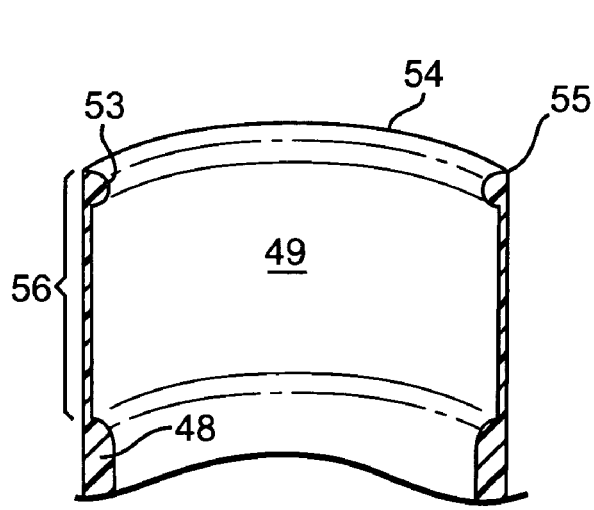
FIG. 3 is a fragmentary, cut-away view of the distal region of the catheter of FIG. 1, having a thin distal wall region and a distal flow restrictor.

FIG. 3 illustrates TPC 54, having distal region 56 with a thinner wall thickness than distal tip 55 or more proximal wall region 48. TPC 54 may also be seen to have a distal tip flow restrictor 53. FIG. 3 illustrates TPC 54 in an unpressurized configuration, where the outer diameter of distal region 56 is substantially similar to that of the average outer diameter of the catheter over its length.

Figure 4:
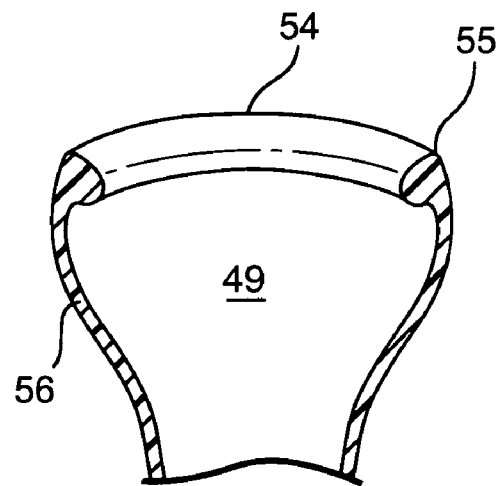
FIG. 4 is a fragmentary, cut-away view, similar to FIG. 3, but shown in a pressurized, radially expanded configuration.

FIG. 4 illustrates TPC 54 in a pressurized configuration, having distal region 56 with an outer diameter substantially larger than that of the outer diameter shown in FIG. 3. In various embodiments, the outer diameter in the expanded state is at least 20%, 40%, 60%, or even 80% larger than that of the unexpanded configuration. FIG. 4 illustrates TPC 54 in a "cobra hood" appearing configuration.

FIG. 5A illustrates a conduit 50 to be used in an end-to-side anastomosis procedure. Conduit 50 includes generally a distal region 51 and a proximal region 53. Conduit 50 is not necessarily drawn to scale. In various embodiments, conduit 50 can be a saphenous vein graft, a radial artery, an internal mammary artery (IMA) having both ends free, a prosthetic artificial conduit (e.g., EPTFE or Dacron), a bioprosthetic conduit (e.g., a xenogenic blood vessel) or any other conduit for which an end-to-side anastomosis is to be performed. In some embodiments, the transconduit perfusion catheter can be used to form an end-to-end anastomosis as well.

The TPC may be too flexible and not sufficiently pushable for some procedures according to the present invention. Therefore, in some methods, a stylet 52 is advanced through conduit 50 to make the conduit stiffer and more pushable. Stylet 52 can be formed of any suitable material, for example, stainless steel or Nitinol. Stylets are well known to those skilled in the art. Stylet 52 can be proximally advanced beginning at conduit distal region 51 in some embodiments, or distally advanced, beginning at conduit proximal region 53 in other embodiments.

FIG. 5B illustrates conduit 50 and stylet 52, after TPC 54 has been advanced over stylet 52 and through conduit 50. In some methods, TPC 54 is advanced proximally, while in other methods, TPC 54 is advanced distally through conduit 50 and over stylet 52. TPC 54 includes distal region 56 as previously described and a proximal region 57. TPC 54 can be positioned such that a couple centimeters of length are exposed beyond the distal end of conduit 50.

FIG. 5C illustrates conduit 50 after stylet 52 has been removed, leaving TPC 54 in place, extending beyond the distal end of conduit 50. TPC may have the proximal end coupled to a controllable blood supply during this procedure.

The TPC can be primed in some methods by filling the TPC with a liquid prior to use. The liquid may be heparinized blood, heparinized saline, or the like. The TPC may have a luer lock connection on the proximal end. In such devices, the liquid can be injected into the TPC to prime the TPC through the luer lock connection. Alternatively, the liquid could be drawn into the TPC through application of suction.

FIG. 5D illustrates conduit 50 carrying TPC 54 being advanced close to a blood vessel 60 having an arteriotomy 64 therein. In the example illustrated, blood vessel 60 has a distal inside diameter within a lumen 61 and a more proximal blockage or stenosis 62. In this example, the normal blood flow direction is given by arrow 63. However, collateral blood flow may be caused in the opposite direction distal of the blockage, indicated by arrow 65. TPC 54 can be advanced through arteriotomy 64 and into blood vessel 60. TPC distal region 56 can be in the unexpanded configuration as the distal region is advanced into blood vessel 60.

FIG. 5E illustrates TPC 54 after distal region 56 has been expanded to have a larger outer diameter, as previously discussed with respect to FIGS. 1 through 4. TPC distal region 56 can expand to form a seal with the inside wall of blood vessel 60 in some devices according to the invention. TPC 54 can thus act to block, eliminate, or significantly reduce the collateral blood flow into the surgical field. Perfusing blood can be supplied via an antegrade cardioplegia needle and TPC 54, indicated at 59. In some methods, the proximal end of TPC 54 (not shown in FIG. 5E) can be coupled to an aortic root needle, which has been used to puncture the aorta, supplying a perfusing blood source. This may be a common source of perfusing blood in an open chest procedure.

In other methods, the proximal end of TPC 54 may be supplied through arterial tubing coupled to the proximal end of TPC 54. This arterial tubing may be supplied from any suitable source, for example, the femoral artery. This may be a source used in closed chest, minimally invasive procedures. The TPC or arterial tubing may be supplied from the femoral artery and inserted into a closed chest through a simple stab wound or port. Any suitable oxygenated fluid can be used to provide the needed oxygen to the blood vessel undergoing the anastomosis. In a preferred embodiment, distal region 56 is expanded within blood vessel 60, and perfusing blood is flowing through distal region 56 to prevent or reduce ischemia while the anastomosis is being performed. The anastomosis is represented by sutures 66 in FIG. 5E. Sutures 66 can be completed entirely around the anastomosis, and sewn completely and tightly to blood vessel 60. In this example, TPC 54 also acts as a suture guide, allowing conduit 50 to be distally advanced over TPC 54 and to blood vessel 60. With the anastomosis completed, TPC 54 can be withdrawn. Any problems in withdrawing TPC 54 may be indicative of an anastomosis that has not been correctly performed, and can indicate a problem in the patency of the just-completed anastomosis.

FIG. 5F illustrates conduit 50 successfully joined to blood vessel 60 with sutures 66. In one method, TPC 54 has the distal region in an unexpanded configuration and reduced in profile to enable easier withdrawal of the catheter through the anastomosis and through conduit 50. With the distal region preferably in the reduced diameter configuration, transconduit perfusion catheter 54 can be withdrawn to proximal region 53 of conduit 50. Once in the proximal location, in some methods, TPC 54 can once again have the distal region expanded radially, to form a seal within proximal region 53 of conduit 50. A purse-string suture 63 may be used to seal TPC 54 within conduit 50. Perfusing blood can once again be supplied through conduit 50 allowing the surgeon to perform other anastomosis. At the appropriate time, proximal region 53 of conduit 50, and any other similar proximal ends of other conduits, may be joined to a permanent, perfusing blood source, for example, the aorta.

Figure 6:
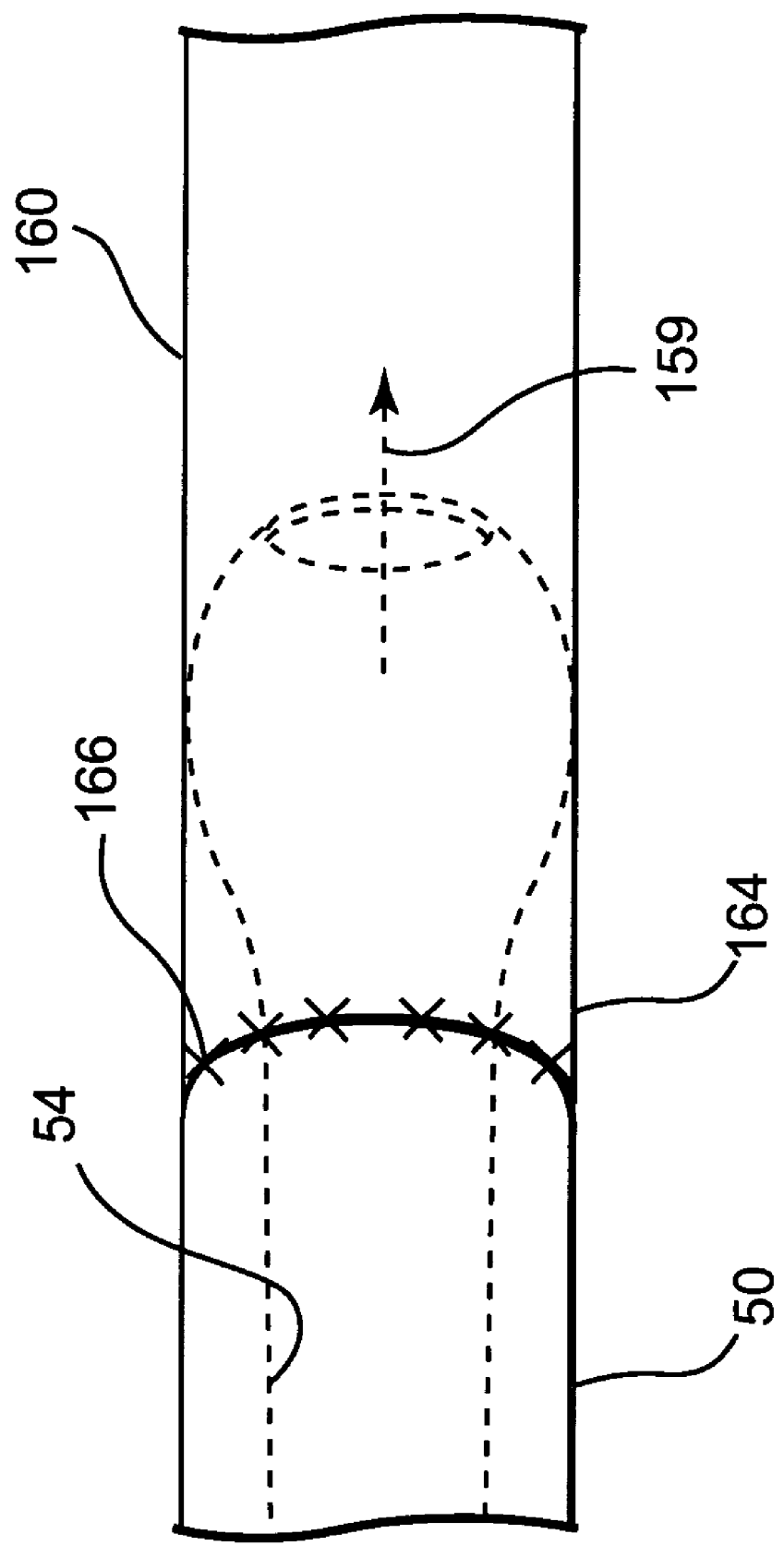
FIG. 6 is a fragmentary, side view an end-to-end anastomosis method according to the present invention, similar is some respects to FIG. 5E.
Figure 7:
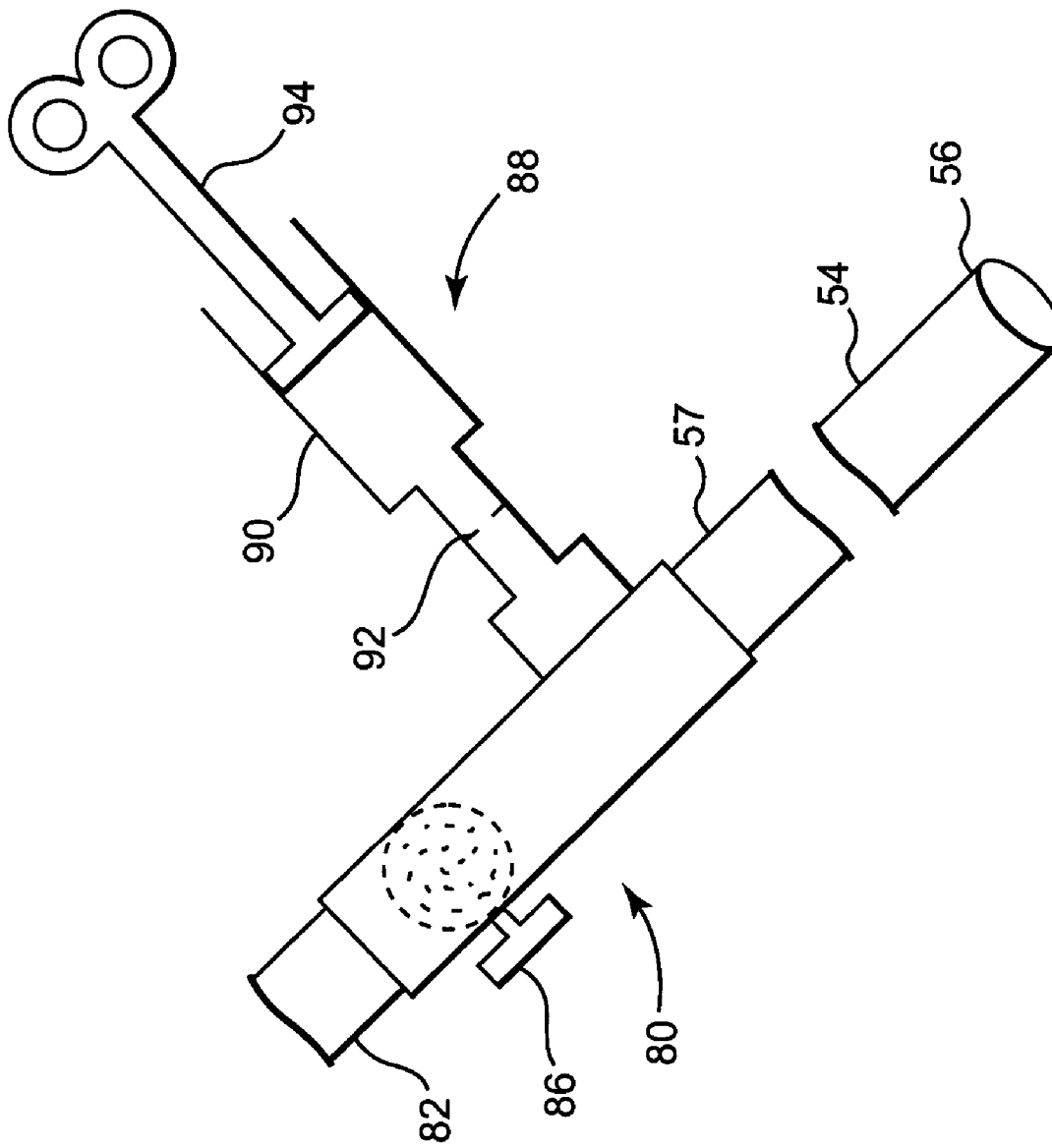
FIG. 7 is a fragmentary, side, highly diagrammatic view of a pressurized blood supply source including a pressure limiting syringe, for supplying the transconduit perfusion catheter with a high pressure source of blood.

FIG. 6 illustrates TPC 54 being used in an end-to-end anastomosis, at a stage similar in some respects to that illustrated in FIG. 5E. TPC 54 been inserted into a proximal end 164 of a blood vessel 160 and expanded to have a larger outer diameter, as previously discussed with respect to FIGS. 1 through 4. Perfusing blood has been delivered via an antegrade cardioplegia needle and TPC 54, indicated at 159. The anastomosis is represented by sutures 166 in FIG. 6. Sutures 166 can be completed entirely around the anastomosis, and sewn completely and tightly to blood vessel 160. In this example, TPC 54 also acts as a suture guide, allowing conduit 50 to be distally advanced over TPC 54 and to blood vessel 160. With the anastomosis completed, TPC 54 can be withdrawn. FIG. 7 illustrates a highly diagrammatic assembly that can be used in some embodiments with TPC 54. An assembly 80 is shown including generally a valve 86 and a pressurized blood source 88. In this example, valve 86 is shown disposed between TPC 54 and a piece of arterial tubing 82. The pressurized blood source can be a manual bulb syringe, a manually operated syringe, or a pressurized or a spring-loaded syringe, which may all optionally have a pressure limiter to limit the pressure of the delivered blood. In the highly diagrammatic example shown in FIG. 7, a syringe 90 is shown having a plunger 94 and a pressure limiter 92. Spring-loaded, pressure limited syringes are known in the art, having been used previously in saphenous vein harvesting.

Figure 8:
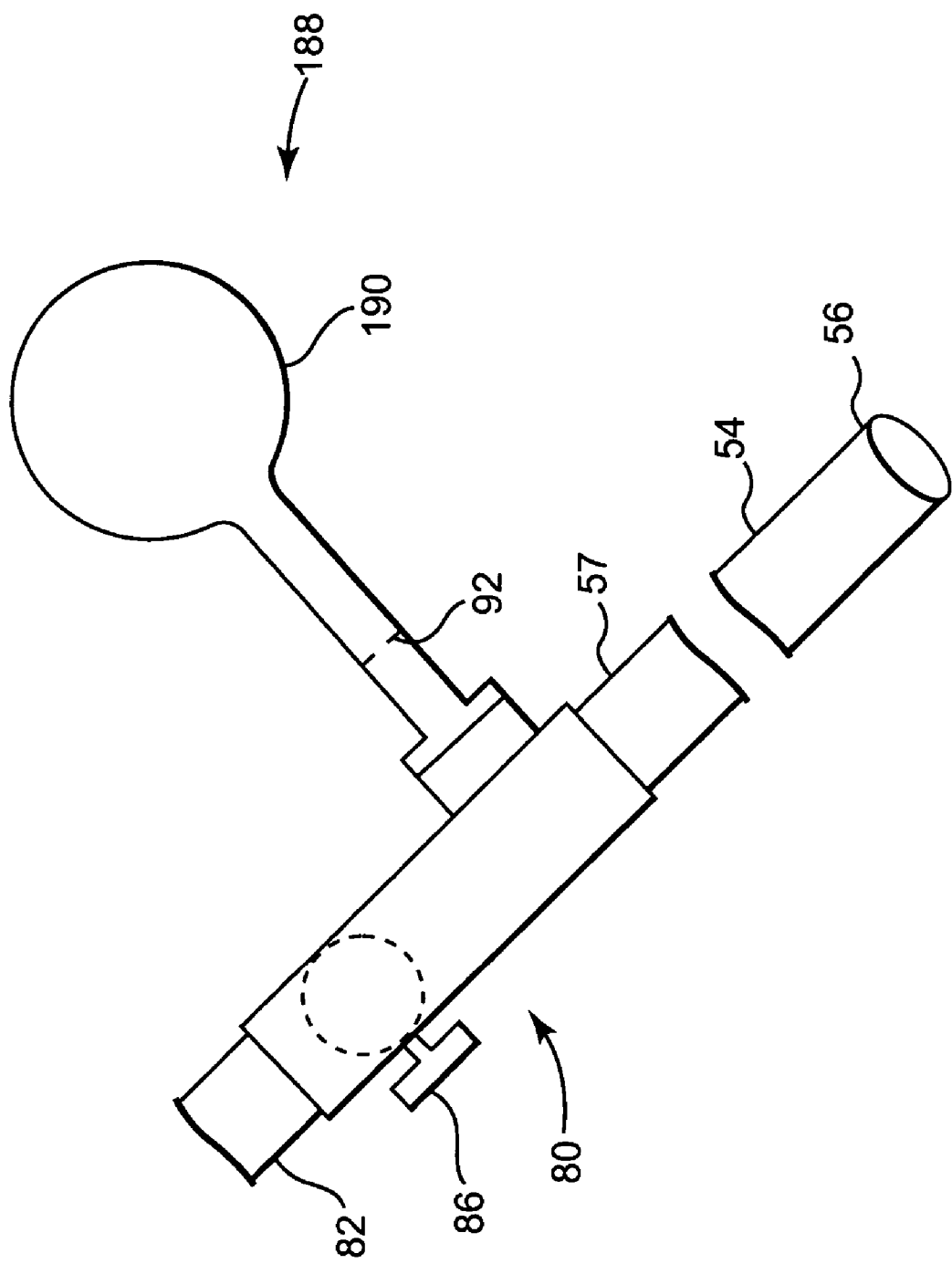
FIG. 8 is a fragmentary, side, highly diagrammatic view of a pressurized blood supply source including a manual squeeze bulb, for supplying the transconduit perfusion catheter with a high pressure source of blood

FIG. 8 illustrates another highly diagrammatic assembly, similar in some respects to that of FIG. 7, and sharing some identically numbered elements that were described with respect to FIG. 7. An assembly 180 is shown including generally valve 86 and a pressurized blood source 188. In this example, valve 86 is shown disposed between TPC 54 and arterial tubing 82. In the highly diagrammatic example shown in FIG. 8, a manual squeeze bulb 190 is shown having pressure limiter 92.

The schematic devices in FIGS. 7 and 8 are not limiting, and are merely intended to illustrate the possibility of a pressure increasing device to provide higher pressure blood than may be possible from the patient's own aorta or femoral artery. In particular, a higher pressure blood source than the patient's blood pressure may be necessary if the patient's blood pressure is too low, or if a higher blood pressure is needed to force blood through the small diameter transconduit perfusion catheter, and past any catheter flow or pressure limiting device, which may be required to expand the outer diameter of the TPC distal region in some devices. Some pressure assist devices have one-way valves distal to, and proximal to, the pressure source, allowing blood to be withdrawn from the patient's aorta and then injected into the blood vessel undergoing the anastomosis.

In addition to blood, therapeutic, diagnostic, and gene therapy agents, can be delivered through the transconduit perfusion catheter. The gene therapy agents, for example, DNA, RNA and packaged DNA and RNA can be delivered through the transconduit perfusion catheter.

All publications, patents and patent documents are incorporated by reference herein, as though individually incorporated by reference. The invention has been described with reference to various specific and preferred embodiments and techniques. However, it should be understood that many various and modifications may be made while remaining within the spirit and scope of the invention.

The invention claimed is:

1. A method for joining a blood conduit having a lumen, distal region, and proximal region, to a blood vessel having a wall, in a patient, the method comprising:
   making an incision in the blood vessel wall;
   inserting a tubular member comprising a tubular wall defining a lumen and having a distal region and a proximal region into the conduit, the tubular member distal region including a flow restrictor and a weakened wall region proximal of the flow restrictor;
   advancing the tubular member distal region into the blood vessel through the incision and then expanding the tubular wall and the lumen of the tubular member distal region radially outward within the blood vessel by forcing oxygenated liquid under pressure through the tubular member to expand the weakened distal region;
   fixedly joining the conduit distal region to the vessel wall near the incision while providing the oxygenated liquid flow from an outlet of the tubular member disposed within the conduit and into the blood vessel; and
   after fixedly joining the conduit to the vessel, withdrawing the tubular member through the conduit.

2. The method of claim 1, in which the inserting is performed before the advancing.

3. The method of claim 1, in which the inserting is performed after the advancing.

4. The method of claim 1, in which the fixedly joining includes suturing the conduit to the blood vessel.

5. The method of claim 1, in which the blood vessel is a coronary artery, the conduit is a saphenous vein, and in which the fixedly joining includes fixedly joining the saphenous vein to the coronary artery.

6. The method of claim 1, in which the blood vessel is a coronary artery, the conduit is an internal mammary artery, and in which the fixedly joining includes fixedly joining the internal mammary artery to the coronary artery.

7. The method of claim 1, in which the oxygenated liquid includes blood.

8. The method of claim 1, in which the oxygenated liquid includes a non-blood oxygenated carrying substance.

9. The method of claim 1, in which the oxygenated liquid includes blood supplied from the patient's femoral artery.

10. The method of claim 1, in which the oxygenated liquid includes blood supplied from the patient's aorta.

11. The method of claim 1, further comprising retracting the tubular member within the conduit and further providing the oxygenated liquid through the tubular member to the conduit proximal region.

12. The method of claim 1, wherein the patient has a blood pressure, wherein the oxygenated liquid is provided at a pressure higher than the patient's blood pressure.

13. The method of claim 12, in which the liquid pressure is provided through a port into the tubular member that is distinct from the proximal end.

14. The method of claim 1, further comprising inserting a stiffening member within the tubular member prior to inserting the tubular member into the conduit.

15. The method of claim 1, further comprising inserting a stiffening member into the tubular member.

16. The method of claim 15, wherein the advancing the tubular member into the blood vessel is performed while the stiffening member is inside the tubular member.

17. A method for joining a blood conduit having a lumen, a distal region, and a proximal region, to a blood vessel having a lumen, a proximal end, and a wall, in a patient, the method comprising:
   inserting a tubular member comprising a tubular wall defining a lumen and having a distal region and a proximal region into and through the conduit, the tubular member distal region including a flow restrictor and a weakened wall region proximal of the flow restrictor;
   advancing the tubular member distal region into the blood vessel lumen through the blood vessel proximal end and then expanding the tubular wall and the lumen of the tubular member distal region radially outward within the blood vessel by forcing oxygenated liquid under pressure through the tubular member to expand the weakened distal region;
   fixedly joining the conduit distal region to the vessel wall near the blood vessel proximal end while providing the oxygenated liquid flow from an outlet of the tubular member disposed within the conduit and into the blood vessel; and
   after fixedly joining the conduit to the vessel, withdrawing the tubular member through the conduit.

18. The method of claim 17, in which the inserting is performed before the advancing.

19. The method of claim 17, in which the inserting is performed after the advancing.

20. The method of claim 17, in which the fixedly joining includes suturing the conduit to the blood vessel.

21. The method of claim 17, in which the blood vessel is a coronary artery, the conduit is a saphenous vein, and in which the fixedly joining includes fixedly joining the saphenous vein to the coronary artery.

22. The method of claim 17, in which the blood vessel is a coronary artery, the conduit is an internal mammary artery, and in which the fixedly joining includes fixedly joining the internal mammary artery to the coronary artery.

23. The method of claim 17, in which the oxygenated liquid includes blood supplied from the patient's femoral artery.

24. The method of claim 17, in which the oxygenated liquid includes blood supplied from the patient's aorta.

25. The method of claim 17, wherein the patient has a blood pressure, wherein the oxygenated liquid is provided at a pressure higher than the patient's blood pressure.

* * * * *